United States Patent
Muraca

(10) Patent No.: US 8,685,891 B2
(45) Date of Patent: *Apr. 1, 2014

(54) METHOD AND ASSAY FOR DETERMINING FAS EXPRESSION

(75) Inventor: Patrick J. Muraca, Pittsfield, MA (US)

(73) Assignee: Nuclea Biotechnologies, Inc., Pittsfield, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/391,910

(22) PCT Filed: Aug. 26, 2010

(86) PCT No.: PCT/US2010/046773
§ 371 (c)(1),
(2), (4) Date: Mar. 9, 2012

(87) PCT Pub. No.: WO2011/031517
PCT Pub. Date: Mar. 17, 2011

(65) Prior Publication Data
US 2012/0165218 A1   Jun. 28, 2012

Related U.S. Application Data

(60) Provisional application No. 61/237,592, filed on Aug. 27, 2009.

(51) Int. Cl.
C40B 30/04 (2006.01)
(52) U.S. Cl.
USPC .......................................................... 506/9
(58) Field of Classification Search
None
See application file for complete search history.

(56) References Cited

U.S. PATENT DOCUMENTS

| 5,665,874 | A | 9/1997 | Kuhadja et al. |
| 5,759,791 | A | 6/1998 | Kuhajda et al. |
| 7,622,260 | B2 | 11/2009 | Gordon et al. |
| 7,732,491 | B2 | 6/2010 | Sherman et al. |
| 7,811,774 | B2 | 10/2010 | Ring et al. |
| 7,906,294 | B2 | 3/2011 | Kinlaw, III |
| 2003/0065156 | A1 | 4/2003 | Williams et al. |
| 2003/0138833 | A1 | 7/2003 | Polyak et al. |
| 2003/0175736 | A1 | 9/2003 | Chinnaiyan et al. |
| 2003/0219760 | A1 | 11/2003 | Gordon et al. |
| 2004/0018546 | A1 | 1/2004 | Hung |
| 2004/0029114 | A1 | 2/2004 | Mack et al. |
| 2005/0196754 | A1 | 9/2005 | Drmanac et al. |

(Continued)

FOREIGN PATENT DOCUMENTS

| WO | 0220736 | 3/2002 |
| WO | 2011031517 | 3/2011 |

OTHER PUBLICATIONS

PCT International Search Report dated Jan. 24, 2011 for International Application No. PCT/US2010/046773.

(Continued)

*Primary Examiner* — Christian Boesen
(74) *Attorney, Agent, or Firm* — DT Ward. P.C.; Donna T. Ward; Lingyun Jia

(57) ABSTRACT

Methods and immunoassays for the determination of fatty acid synthase (FAS) expression in patients having or suspected of having a proliferative disorder, especially prostate cancer, are disclosed. The sensitive method and assay detect the level of expression of FAS in a biological sample using antibodies that are highly specific for FAS. The method and assay can be used to monitor the progression of cancer, and/or to predict the efficacy of certain treatments or the likelihood of recurrence of the cancer.

5 Claims, 4 Drawing Sheets

(56) References Cited

U.S. PATENT DOCUMENTS

| | | |
|---|---|---|
| 2006/0034850 A1 | 2/2006 | Weidanz et al. |
| 2007/0148718 A1 | 6/2007 | Medghalchi et al. |
| 2007/0207975 A1 | 9/2007 | Menendez et al. |
| 2008/0050278 A1 | 2/2008 | Farina et al. |
| 2008/0056553 A1 | 3/2008 | Rimm et al. |
| 2008/0103208 A1 | 5/2008 | Ossovskaya et al. |
| 2009/0104617 A1 | 4/2009 | Gordon et al. |
| 2009/0232818 A1 | 9/2009 | Kinlaw, III |
| 2009/0304679 A1 | 12/2009 | Weidanz |
| 2010/0158894 A1 | 6/2010 | Umemura et al. |
| 2011/0059854 A1 | 3/2011 | Gordon et al. |
| 2011/0124021 A1 | 5/2011 | Medghalchi |
| 2011/0150876 A1 | 6/2011 | Kinlaw, III |
| 2011/0195411 A1 | 8/2011 | Cao |
| 2011/0237625 A1 | 9/2011 | Gaul et al. |
| 2012/0065107 A1 | 3/2012 | Ring et al. |
| 2012/0301467 A1 | 11/2012 | Medghalchi et al. |

OTHER PUBLICATIONS

Alo, et al. Immunohistochemical expression of human enrythrocyte glucose transporter and fatty acid synthase in infiltrating breast carcinomas and adjacent typical/atypical hyperplastic or normal breast tissue. Am J Clin Pathol. 2001, 116(1): 129-134.

Yang, et al. "Activity-based proteome profiling of potential cellular targets of Orlistat—an FDA-approved drug with anti-tumor activities." J Am Chem Soc. 2010, 132(2): 655-666; p. 656-666.

Camassei, et al. "Expression of the Lipogenic Enzyme Fatty Acid Synthase (FAS) in Retinoblastoma and Its Correlation with Tumor Aggressiveness." Invest Ophthalmol Vis Sci. 2003, 44(6) pp. 2399-2403.

Bloom, et al. "Histological grading and prognosis in breast cancer; a study of 1409 cases of which 359 have been followed for 15 years." Br J Cancer. 1957, 11(3): 359-377.

Campa, et al. "Genetic variation in genes of the fatty acid synthesis pathway and breast cancer risk." Breast Cancer Res Treat. 2009, 118(3): 565-574.

Wang, et al. "Fatty acid synthase (FAS) expression in human breast cancer cell culture supernatants and in breast cancer patients." Cancer Lett. 2001, 167(1): 99-104.

Wang, et al "Two-site ELISA for the quantitative determination of fatty acid." Clinica Chimica Acta 2001, 304: 107-115.

Sorlie, et al. "Distinct molecular mechanisms underlying clinically relevant subtypes of breast cancer: gene expression analyses across three different platforms." BMC Genomics 2006, 7: 127, pp. 1-15.

International Search Report for International Application No. PCT/US2012/060187, dated Apr. 15, 2013.

International Preliminary Report on Patentability (IPRP) dated Mar. 8, 2012 for International Application No. PCT/US2010/046773.

US 8,685,891 B2

METHOD AND ASSAY FOR DETERMINING FAS EXPRESSION

RELATED APPLICATIONS

This application is a 35 U.S.C. §371 U.S. National Phase Entry of International Application No. PCT/US2010/046773 filed Aug. 26, 2010, and which claims the benefit of priority of U.S. provisional application Ser. No. 61/237,592, filed Aug. 27, 2009, the entirety of which is incorporated herein by reference.

REFERENCE TO SEQUENCES

The instant application contains a Sequence Listing which has been submitted in ASCII format via EFS-Web and is hereby incorporated by reference in its entirety. Said ASCII copy, created on Feb. 23, 2012 which is 1,555 bytes in size, is named NUC036US_SEQLST_final.

TECHNICAL FIELD

The present invention relates to antibodies and related molecules that immunospecifically bind to fatty acid synthase and related pathway proteins, and their use in immunoassays for fatty acid synthase activity. The invention relates to methods and assays for detecting, screening, diagnosing or determining the progression of a proliferative disease or pre-cancerous condition using the present antibodies and assays.

BACKGROUND ART

Fatty acid synthase (FAS) is a 270 kDa cytosolic protein that functions as a homodimer. (1) FAS is expressed in low to undetectable levels in most normal human tissues. (2) In contrast, FAS is overexpressed in a large number of human cancers, including prostate cancer, despite high levels of ambient fatty acids, and its overexpression has been associated with poor prognosis. (3-6) In prostate cancer, FAS is overexpressed throughout the natural history of a majority of tumors beginning with prostatic intraepithelial neoplasia (PIN). (3) Although the biochemical and metabolic basis for FAS overexpression in tumor cells in not well understood, it appears that FAS overexpression confers a selective growth advantage to tumor cells. Prostate tumors expressing high FAS levels display aggressive biologic behavior. (7)(8)

Prostate-specific antigen (PSA) is used as a biological or tumor marker to detect prostate disease. PSA is a protein produced by cells of the prostate gland. The PSA test measures the level of PSA in the blood; but PSA alone is not a reliable indicator of the presence of prostate disease.

It is normal for men to have a low level of PSA in their blood. The reference range of PSA is between 0-4.0 ng/mL, based on a study that found 99% of a cohort of apparently healthy men had a total PSA level below 4 ng/mL; the upper limit of normal is much less than 4 ng/mL. (9)(10) Increased levels of PSA may suggest the presence of prostate cancer; however, prostate cancer can also be present in the complete absence of an elevated PSA level, in which case the test result would be a false negative. (9)

As men age, both benign prostate conditions and prostate cancer become more common, resulting in an increase in PSA levels. PSA levels can be increased by conditions including prostate infection, irritation or benign prostatic hyperplasia (BPH). (11)(12) According to the National Cancer Institute, PSA levels alone do not give doctors enough information to distinguish between benign prostate conditions and cancer. Treatment needs to be individualized based on the individual's risk of progression as well as the likelihood of success and the risks of the treatment. (13)

SUMMARY OF THE INVENTION

The invention comprises methods, compositions and kits for the rapid and accurate identification of fatty acid synthase (FAS) expression in patients having or suspected of having a proliferative disorder or pre-cancerous condition characterized by FAS overexpression. The present method comprises determining the level of expression of the FAS gene or protein in biological sample of a patient having or suspected of having prostate cancer, prostatic intraepithelial neoplasia (PIN), or another proliferative disorder or pre-cancerous condition using monoclonal or polyclonal antibodies that are highly specific for FAS.

The present method generally comprises the following steps: (a) obtaining a biological sample containing cancer cells from a patient; (b) contacting the sample with antibodies specific for FAS; (c) detecting the presence and amount of FAS conjugated with the antibodies; and (d) correlating the amount of FAS with the presence or aggressiveness of the cancer or pre-cancerous condition, the likelihood that the cancer will recur, and/or the likelihood that the cancer will respond to therapeutic treatment.

The assay of the present invention utilizes novel antibodies that are highly specific for human FAS. The antibodies may be polyclonal or monoclonal, and may be used as capture and/or detection antibodies in an immunoassay. In a currently preferred embodiment, the antibodies are monoclonal antibodies raised against FAS peptides derived from sections of human FAS protein having the least homology with non-human FAS.

Any type of immunoassay format may be employed, including enzyme-linked immunoassays (ETA, ELISA), Western blot, Dot blot, radioimmunoassay (RIA), agglutination, flow cytometry, or other formats. In a preferred embodiment, the present assay employs a sandwich-ELISA technique to measure the level of FAS in cells circulating in a bodily fluid, such as human serum or plasma. In this embodiment, the anti-FAS antibodies of the invention are used as capture antibodies.

The kit of the invention comprises, at a minimum, (a) a substrate having anti-FAS antibodies immobilized thereon; and (b) detection antibodies tagged with a detectable moiety. The kit may further comprise contain reagents, e.g., for cell lysis and/or washing.

The present invention can be used for monitoring of disease progression for proliferative disorders characterized by the overexpression of FAS, especially prostate cancer, and for predicting the efficacy of certain therapeutic agents for treating such disorders. The present method and assay provides a more sensitive and more accurate prognostic tool than PSA for monitoring prostate cancer, and may be used in place of or in conjunction with PSA tests to monitor prostate cancer. In one aspect, the present method and kit can be used to predict the efficacy of therapeutic approaches, such as androgen ablation.

DETAILED DESCRIPTION OF THE INVENTION

Figure 1:
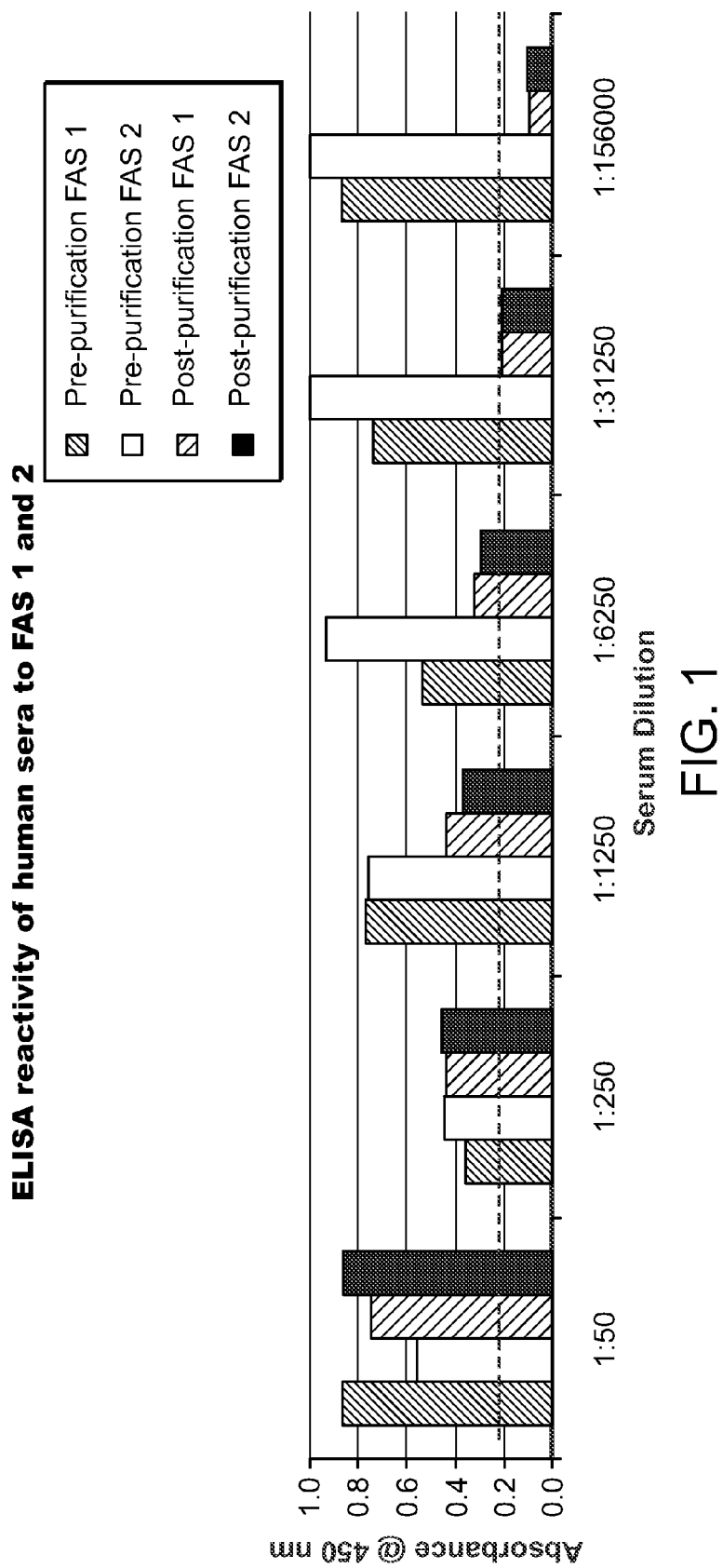
FIG. 1 is a graph showing the results of an ELISA assay using monoclonal antibodies of the present invention raised against the peptide of SEQ. ID NOs. 1 and 2 as the capture antibody. For each dilution, the two left columns represent the pre-purification MAbs, and the two right columns represent the post-purification MAbs.

The present invention comprises methods, compositions and kits for the rapid and accurate identification of FAS expression in cells. FAS is overexpressed in a number of proliferative disorders, including prostate cancer, and pre-cancerous conditions, such as PIN.

The present method generally comprises the following steps: (a) obtaining a biological sample containing cancer cells from a patient; (b) contacting the sample with antibodies specific for FAS; (c) detecting the presence and amount of FAS conjugated with the antibodies; and (d) correlating the amount of FAS with the presence of PIN, the aggressiveness of prostate cancer, the likelihood that the cancer will recur, and/or the likelihood that the cancer will respond to therapeutic treatment. The biological sample may be cells or tissue, and preferably is serum or plasma containing cells. However, the cells also may be obtained from tissue samples or cell cultures.

FAS from cancer cells can be detected in circulating cancer cells in a blood sample. In a preferred embodiment, the present invention provides a method of detecting the expression of FAS from cancer cells in a blood sample comprising removing the red blood cells from the blood sample thereby localizing the cancer cells in the blood serum, lysing the cancer cells in the serum, followed by performing on the serum containing the lysed cells an immunoassay capable of detecting FAS.

The present assays and methods are sensitive enough for quantifying the levels of FAS in circulating cancer cells in blood samples. The present invention provides methods for identifying those cancer patients who are likely to benefit from certain anticancer therapies (including, but not limited to, FAS-targeted therapies). A convenient, highly sensitive and rapid means to test blood samples to identify additional patients who would benefit from such therapies would be an important advance in the cancer treatment field. As indicated below, a rapid and highly sensitive immunological assay to detect FAS proteins in circulating cancer cells.

This invention is based on combining the high specificity of procedures used to isolate circulating cancer cells from blood with the high sensitivity of certain immunologically based assays. Circulating cancer cells preferably are first concentrated in the serum or plasma by treating the blood sample to remove red cells. One preferred method uses centrifugation to remove red cells, thereby isolating the circulating cancer cells in the blood serum or plasma. Another preferred method of enrichment of cancer cells consists of collecting a whole blood sample followed by the lysis of red blood cells. The currently preferred method comprises collecting a whole blood sample in a cell preparation tube (such as the BD VACUTAINER® CPT, Becton Dickinson) and obtaining by centrifugation a peripheral blood mononuclear fraction that contains enriched cancer cells.

The antibodies used in the present invention for detection or capture of FAS are novel anti-FAS antibodies that are highly specific for human FAS. In a preferred embodiment, the present antibodies are monoclonal antibodies specific for a human FAS sequence selected from SEQ ID NOs. 1-5. In a preferred embodiment, the present antibodies are used as capture antibodies in a sandwich ELISA assay.

Anti-FAS Antibodies

The assays of the present invention utilizes novel antibodies that are highly specific for human FAS. The antibodies may be polyclonal or monoclonal, and may be used as capture and/or detection antibodies in an immunoassay. In a currently preferred embodiment, the antibodies are monoclonal antibodies raised against FAS peptides derived from sections of human FAS protein having the least homology with non-human FAS.

The present antibodies comprise polyclonal or monoclonal antibodies, or antibody fragments, that immunospecifically bind to a FAS protein, fragment or a variant of FAS, as well as certain FAS related pathway proteins. In particular, the invention encompasses antibodies or fragments thereof that immunospecifically bind to a FAS protein comprising at least about six consecutive amino acids up to the full length of any of the polypeptides of SEQ ID NOs. 1-5.

The antibodies of the present invention also comprise non-human monoclonal antibodies (e.g., murine, rabbit or goat) and polyclonal antisera that bind to FAS or variants thereof comprising at least a portion of the sequence of a peptide of SEQ ID NO. 1-5. In preferred aspect, the antibodies are human or humanized monoclonal antibodies. The antibodies of the present invention further encompass fragments or variants of these antibodies (e.g., VH domains, VH CDRs, VL domains, or VL CDRs), that immunospecifically bind to FAS or variants thereof comprising at least a portion of the sequence of a peptide of SEQ ID NO. 1-5. The present antibodies or fragments thereof also may bind to certain FAS-related proteins that contain at least a portion of the sequence of a peptide of SEQ ID NO. 1-5.

The antibodies of the present invention can be produced by using well-established techniques for producing monoclonal and polyclonal antibodies, using the FAS peptides of SEQ ID NO. 1-5 as immunogens. In a preferred embodiment, the FAS peptide contains an amino acid sequence that is identical with or homologous to all or a portion containing at least about six consecutive amino acids of a sequence represented by any one of SEQ ID NOs. 1-5. A homologous sequence is at least about 70%, 75%, 80%, 85%, 90% or 95% identical to the peptide represented by any one of SEQ ID NOs. 1-5, wherein X represents any naturally occurring amino acid.

FAS Peptides:

SEQ ID NO. 1
VAQGQWEPSGXAP

SEQ ID NO. 2
PSGPAPTNXGALE

TLEQQHXVAQGQW SEQ ID NO. 3

EVDPGSAELQKVLQGD SEQ ID NO. 4

ELSSKADEASELAC SEQ ID NO. 5

FAS peptides can be synthesized by methods well known in the art. Synthetic methods that can be used include, for example, ribosomally-directed fermentation methods, as well as non-ribosomal strategies and chemical synthesis methods. Methods for making the peptides are described in co-pending PCT application no. PCT/US10/30545, filed Apr. 9, 2010, the entirety of which is hereby incorporated herein by reference.

As used herein, the term "antibody" refers to an immunoglobulin specifically immunoreactive to a given antigen (e.g., a FAS peptide of the invention). The term "antibody" as used herein is intended to include whole antibodies of any isotype (IgG, IgA, IgM, IgE, etc), and fragments thereof. An "antibody" of the invention also includes an antibody preparation, e.g., a serum (antiserum). Antibodies can be fragmented using conventional techniques and the fragments screened for utility in the same manner as whole antibodies. Thus, the term includes segments of proteolytically-cleaved or recombinantly-prepared portions of an antibody molecule that selectively reacts with a certain protein or peptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies may be labeled with detectable labels by one of skill in the art. The label can be a radioisotope, fluorescent compound, chemiluminescent compound, enzyme, or enzyme co-factor, or any other labels known in the art. In some aspects, the antibody that binds to an entity one wishes to measure (the primary antibody) is not labeled, but is instead detected by binding of a labeled secondary antibody that specifically binds to the primary antibody.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the invention can be from any animal origin including birds and mammals. Preferably, the antibodies are of human, murine (e.g., mouse and rat), donkey, sheep, rabbit, goat, guinea pig, camel, horse, or chicken origin.

As used herein, a "monoclonal antibody" refers to an antibody that recognizes only one type of antigen. This type of antibodies is produced by the daughter cells of a single antibody-producing hybridoma. A monoclonal antibody typically displays a single binding affinity for any epitope with which it immunoreacts. A monoclonal antibody may contain an antibody molecule having a plurality of antibody combining sites, each immunospecific for a different epitope, e.g., a bispecific monoclonal antibody. Monoclonal antibodies may be obtained by methods known to those skilled in the art. Kohler and Milstein (1975), Nature, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), Antibodies: A Laboratory Manual, Cold Spring Harbor Laboratory; Colligan et al. (1992, 1993), eds., Current Protocols in Immunology, Greene Publishing Assoc. and Wiley Interscience, N.Y.; Iyer et al., Ind. J. Med. Res., (2000), 123:561-564.

The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. See, e.g., WO 93/17715; WO 92/08802; WO 91/00360; WO 92/05793; Tuft et al., 1991, J. Immunol., 147:60-69; U.S. Pat. Nos. 4,474,893; 4,714,681; 4,925,648; 5,573,920; 5,601,819; and Kostelny et al., 1992, J. Immunol., 148:1547-1553. For example, the antibodies may be produced against a peptide containing repeated units of a FAS peptide sequence of the invention, or they may be produced against a peptide containing two or more FAS peptide sequences of the invention, or the combination thereof.

Moreover, antibodies can also be prepared from any region of the FAS peptides of the invention. In addition, if a polypeptide is a receptor protein, antibodies can be developed against an entire receptor or portions of the receptor, for example, an intracellular domain, an extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example.

In the present invention, the FAS peptides for generating antibodies preferably contain a sequence of at least about 6, at least about 7, more preferably at least about 8, at least about 9, at least about 10, at least about 11, at least about 12, at least about 13, and preferably, between about 5 to about 50 amino acids in length, more preferably between about 8 to about 15 amino acids in length. The preferred FAS peptides are those having an amino acid sequence the same as or homologous to all or a portion of the sequence of the peptides of SEQ ID NOs. 1-5.

The human, humanized or non-human monoclonal antibodies of the present invention can be prepared using well-established methods. In one embodiment, the monoclonal antibodies are prepared using hybridoma technology, such as those described by Kohler and Milstein (1975), Nature, 256: 495. In a hybridoma method, a mouse, hamster, or other appropriate host animal, is typically immunized with an immunizing agent (e.g., a FAS peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell. Goding, Monoclonal Antibodies: Principles and Practice, Academic Press, (1986) pp. 59-1031. Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.* (1984), 133:3001; Brodeur et al., Monoclonal Antibody Production Techniques and Applications, Marcel Dekker, Inc., New York, (1987) pp. 51-63; Fukuma et al., *Autoimmunity*, 10(4):291-195 (1991).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding specificity of the monoclonal antibody can, for example, be determined by the Scatchard analysis of Munson and Pollard (1980), *Anal. Biochem.*, 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see, U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Polyclonal antibodies of the invention can also be produced by various procedures well known in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100 µg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Antibodies encompassed by the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv, or disulfide stabilized antibody domains recombinantly fused to either the phage polynucleotide III or polynucleotide VIII protein. Examples of phage display methods that can be used to make the antibodies of the present invention include those disclosed in Brinkman et al. (1995) *J. Immunol. Methods*, 182:41-50; Ames et al. (1995) *J. Immunol. Methods*, 184:177-186; Kettleborough et al. (1994) *Eur. J. Immunol.*, 24:952-958; Persic et al. (1997) *Gene*, 187:9-18; Burton et al. (1994) *Advances in Immunology*, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce antibody fragments such as single-chain Fvs and antibodies include those described in U.S. Pat. Nos. 4,946,778 and 5,258,498; Huston et al. (1991) *Methods in Enzymology*, 203: 46-88; Shu et al. (1993) *Proc. Natl. Acad. Sci. USA*, 90:7995-7999; and Skerra et al. (1988) *Science*, 240:1038-1040, each of which is incorporated herein by reference in its entirety.

For some uses, including the in vivo use of antibodies in humans and in vitro detection assays, it is preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. See, e.g., Morrison (1985), Science, 229: 1202; Oi et al. (1986), BioTechniques, 4:214; Gillies et al. (1989), J. Immunol. Methods, 125:191-202; and U.S. Pat. Nos. 5,807,715; 4,816,567; and 4,816,397, which are incorporated herein by reference in their entirety.

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. See, e.g., Queen et al., U.S. Pat. Nos. 5,693,762 and 5,585,089; and Riechmann et al. (1988) Nature, 332:323, which are incorporated herein by reference in their entireties. Antibodies can be humanized using a variety of techniques known in the art, including, for example, CDR-grafting (EP 239, 400; PCT publication WO 91/09967; U.S. Pat. Nos. 5,225,539; 5,530,101; and 5,585,089); veneering or resurfacing (EP 592,106; EP 519,596; Padlan (1991), *Molecular Immunology*, 28(4/5):489-498; Studnicka et al. (1994) *Protein Engineering*, 7(6):805-814; Roguska et al. (1994) *Proc. Natl. Acad. Sci. USA*, 91:969-973; and chain shuffling (U.S. Pat. No. 5,565,332). A currently preferred method for making humanized monoclonal antibodies of the present invention are the methods described by Le et al., *Cell Cycle*, 4(1):87-95 (2005) and Carter et al., *Proc. Natl. Acad. Sci. USA*, 89:4285-89 (1992), which are incorporated herein by reference.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (1995) *Intl. Rev. Immunol.*, 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies. Preferred methods for producing human monoclonal antibodies of the present invention are those described in Nash et al., *Immunology*, 68:332-340 (1989) and Fukuma et al., *Autoimmunity*, 10(4):291-195 (1991).

Once an antibody molecule of the invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In one embodiment, the present invention provides human or humanized monoclonal antibodies that specifically immuoreact to a FAS protein, or fragment or variant thereof. In a preferred embodiment, the invention provides a novel monoclonal antibody that specifically recognizes a sequence comprising at least about 6 up to the entire sequence of a peptide selected from the group consisting of SEQ ID NOs. 1-5.

Assays

The term "immunoassay" refers to a test that uses the binding of antibodies to antigens to identify and measure certain substances. Immunoassays often are used to diagnose disease, and test results can provide information about a disease that may help in planning treatment (for example, when estrogen receptors are measured in breast cancer). An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity.

The immunoassays of the present invention utilize the ant-FAS polyclonal or monoclonal antibodies described herein to specifically bind to FAS in a biological sample. Any type of immunoassay format may be used, including, without limitation, enzyme immunoassays (EIA, ELISA), radioimmunoassay (RIA), fluoroimmunoassay (FIA), chemiluminescent immunoassay (CLIA), counting immunoassay (CIA), immunohistochemistry (IHC), agglutination, nephelometry, turbidimetry or Western Blot. These and other types of immunoassays are well-known and are described in the literature, for example, in Immunochemistry, Van Oss and Van Regenmortel (Eds), CRC Press, 1994; The Immunoassay Handbook, D. Wild (Ed.), Elsevier Ltd., 2005; and the references disclosed therein.

The preferred assay format for the present invention is the enzyme-linked immunosorbent assay (ELISA) format. ELISA is a highly sensitive technique for detecting and measuring antigens or antibodies in a solution in which the solution is run over a surface to which immobilized antibodies specific to the substance have been attached, and if the substance is present, it will bind to the antibody layer, and its presence is verified and visualized with an application of antibodies that have been tagged or labeled so as to permit detection. ELISAs combine the high specificity of antibodies with the high sensitivity of enzyme assays by using antibodies or antigens coupled to an easily assayed enzyme that possesses a high turnover number such as alkaline phosphatase (AP) or horseradish peroxidase (HRP), and are very useful tools both for determining antibody concentrations (antibody titer) in sera as well as for detecting the presence of antigen.

There are many different types of ELISAs; the most common types include "direct ELISA," "indirect ELISA," "sandwich ELISA" and cell-based ELISA (C-ELISA). Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate typically is washed with a mild detergent solution to remove any proteins or antibodies that are not specifically bound. After the final wash step the plate is developed by adding an enzymatic substrate tagged with a detectable label to produce a visible signal, which indicates the quantity of antigen in the sample.

In a typical microtiter plate sandwich immunoassay, an antibody ("capture antibody") is adsorbed or immobilized onto a substrate, such as a microtiter plate. Monoclonal antibodies are preferred as capture antibodies due to their greater specificity, but polyclonal antibodies also may be used. When the test sample is added to the plate, the antibody on the plate will bind the target antigen from the sample, and retain it in the plate. When a second antibody ("detection antibody") or antibody pair is added in the next step, it also binds to the target antigen (already bound to the monoclonal antibody on the plate), thereby forming an antigen 'sandwich' between the two different antibodies.

This binding reaction can then be measured by radio-isotopes, as in a radio-immunoassay format (RIA); by enzymes, as in an enzyme immunoassay format (EIA or ELISA); or other detectable label, attached to the detection antibody. The label generates a color signal proportional to the amount of target antigen present in the original sample added to the plate. Depending on the immunoassay format, the degree of color can be detected and measured with the naked eye (as with a home pregnancy test), a scintillation counter (for an RIA), or with a spectrophotometric plate reader (for an EIA or ELISA).

The assay then is carried out according to the following general steps:

Step 1: Capture antibodies are adsorbed onto the well of a plastic microtiter plate (no sample added);

Step 2: A test sample (such as human serum) is added to the well of the plate, under conditions sufficient to permit binding of the target antigen to the capture antibody already bound to the plate, thereby retaining the antigen in the well;

Step 3: Binding of a detection antibody or antibody pair (with enzyme or other detectable moiety attached) to the target antigen (already bound to the capture antibody on the plate), thereby forming an antigen "sandwich" between the two different antibodies. The detectable label on the detection antibodies will generate a color signal proportional to the amount of target antigen present in the original sample added to the plate.

In an alternative embodiment, sometimes referred to as an antigen-down immunoassay, the analyte (rather than an antibody) is coated onto a substrate, such as a microtiter plate, and used to bind antibodies found in a sample. When the sample is added (such as human serum), the antigen on the plate is bound by antibodies (IgE for example) from the sample, which are then retained in the well. A species-specific antibody (anti-human IgE for example) labeled with an enzyme such as horse radish peroxidase (HRP) is added next, which, binds to the antibody bound to the antigen on the plate. The higher the signal, the more antibodies there are in the sample.

In another embodiment, an immunoassay may be structured in a competitive inhibition format. Competitive inhibition assays are often used to measure small analytes because competitive inhibition assays only require the binding of one antibody rather than two as is used in standard ELISA formats. In a sequential competitive inhibition assay, the sample and conjugated analyte are added in steps similar to a sandwich assay, while in a classic competitive inhibition assay, these reagents are incubated together at the same time.

In a typical sequential competitive inhibition assay format, a capture antibody is coated onto a substrate, such as a microtiter plate. When the sample is added, the capture antibody captures free analyte out of the sample. In the next step, a known amount of analyte labeled with a detectable label, such as an enzyme or enzyme substrate, added. The labeled analyte also attempts to bind to the capture antibody adsorbed onto the plate, however, the labeled analyte is inhibited from binding to the capture antibody by the presence of previously bound analyte from the sample. This means that the labeled analyte will not be bound by the monoclonal on the plate if the monoclonal has already bound unlabeled analyte from the sample. The amount of unlabeled analyte in the sample is inversely proportional to the signal generated by the labeled analyte. The lower the signal, the more unlabeled analyte there is in the sample. A standard curve can be constructed using serial dilutions of an unlabeled analyte standard. Subsequent sample values can then be read off the standard curve as is done in the sandwich ELISA formats. The classic competitive inhibition assay format requires the simultaneous addition of labeled (conjugated analyte) and unlabeled analyte (from the sample). Both labeled and unlabeled analyte then compete simultaneously for the binding site on the monoclonal capture antibody on the plate. Like the sequential competitive inhibition format, the colored signal is inversely proportional to the concentration of unlabeled target analyte in the sample. Detection of labeled analyte can be read on a microtiter plate reader.

In addition to microtiter plates, immunoassays are also may be configured as rapid tests, such as a home pregnancy test. Like microtiter plate assays, rapid tests use antibodies to react with antigens and can be developed as sandwich formats, competitive inhibition formats, and antigen-down formats. With a rapid test, the antibody and antigen reagents are bound to porous membranes, which react with positive samples while channeling excess fluids to a non-reactive part of the membrane. Rapid immunoassays commonly come in two configurations: a lateral flow test where the sample is simply placed in a well and the results are read immediately;

and a flow through system, which requires placing the sample in a well, washing the well, and then finally adding an analyte-detectable label conjugate and the result is read after a few minutes. One sample is tested per strip or cassette. Rapid tests are faster than microtiter plate assays, require little sample processing, are often cheaper, and generate yes/no answers without using an instrument. However, rapid immunoassays are not as sensitive as plate-based immunoassays, nor can they be used to accurately quantitate an analyte.

The preferred technique for use in the present invention to detect the amount of FAS in circulating cells is the sandwich ELISA, in which highly specific monoclonal antibodies are used to detect sample antigen. The sandwich ELISA method comprises the following general steps:

1. Prepare a surface to which a known quantity of capture antibody is bound;
2. (Optionally) block any non specific binding sites on the surface;
3. Apply the antigen-containing sample to the surface;
4. Wash the surface, so that unbound antigen is removed;
5. Apply primary (detection) antibodies that bind specifically to the bound antigen;
6. Apply enzyme-linked secondary antibodies which are specific to the primary antibodies;
7. Wash the plate, so that the unbound antibody-enzyme conjugates are removed;
8. Apply a chemical which is converted by the enzyme into a detectable (e.g., color or fluorescent or electrochemical) signal; and
9. Measure the absorbance or fluorescence or electrochemical signal to determine the presence and quantity of antigen.

In an alternate embodiment, the primary antibody (step 5) is linked to an enzyme; in this embodiment, the use of a secondary antibody conjugated to an enzyme (step 6) is not necessary if the primary antibody is conjugated to an enzyme. However, use of a secondary-antibody conjugate avoids the expensive process of creating enzyme-linked antibodies for every antigen one might want to detect. By using an enzyme-linked antibody that binds the Fc region of other antibodies, this same enzyme-linked antibody can be used in a variety of situations. The major advantage of a sandwich ELISA is the ability to use crude or impure samples and still selectively bind any antigen that may be present. Without the first layer of "capture" antibody, any proteins in the sample (including serum proteins) may competitively adsorb to the plate surface, lowering the quantity of antigen immobilized.

In a currently preferred embodiment of the present invention, a solid phase substrate, such as a microtiter plate or strip, is treated in order to fix or immobilize a capture antibody to the surface of the substrate. The material of the solid phase is not particularly limited as long as it is a material of a usual solid phase used in immunoassays. Examples of such material include polymer materials such as latex, rubber, polyethylene, polypropylene, polystyrene, a styrene-butadiene copolymer, polyvinyl chloride, polyvinyl acetate, polyacrylamide, polymethacrylate, a styrene-methacrylate copolymer, polyglycidyl methacrylate, an acrolein-ethyleneglycol dimethacrylate copolymer, polyvinylidene difluoride (PVDF), and silicone; agarose; gelatin; red blood cells; and inorganic materials such as silica gel, glass, inert alumina, and magnetic substances. These materials may be used singly or in combination of two or more thereof.

The form of the solid phase is not particularly limited insofar as the solid phase is in the form of a usual solid phase used in immunoassays, for example in the form of a microtiter plate, a test tube, beads, particles, and nanoparticles. The particles include magnetic particles, hydrophobic particles such as polystyrene latex, copolymer latex particles having hydrophilic groups such as an amino group and a carboxyl group on the surfaces of the particles, red blood cells and gelatin particles. The solid phase is preferably a microtiter plate or strip, such as those available from Cell Signalling Technology, Inc.

The capture antibody preferably is one or more monoclonal anti-FAS antibodies described herein that specifically bind to at least a portion of one or more of the peptide sequences of SEQ ID NO. 1-5. Where microtiter plates or strips are used, the capture antibody is immobilized within the wells. Techniques for coating and/or immobilizing proteins to solid phase substrates are known in the art, and can be achieved, for example, by a physical adsorption method, a covalent bonding method, an ionic bonding method, or a combination thereof. See, e.g., W. Luttmann et al., *Immunology*, Ch. 4.3.1 (pp. 92-94), Elsevier, Inc. (2006) and the references cited therein. For example, when the binding substance is avidin or streptavidin, a solid phase to which biotin was bound can be used to fix avidin or streptavidin to the solid phase. The amounts of the capture antibody, the detection antibody and the solid phase to be used can also be suitably established depending on the antigen to be measured, the antibody to be used, and the type of the solid phase or the like. Protocols for coating microtiter plates with capture antibodies, including tools and methods for calculating the quantity of capture antibody, are described for example, on the websites for Immunochemistry Technologies, LLC (Bloomington, Minn.) and Meso Scale Diagnostics, LLC (Gaithersburg, Md.).

The detection antibody can be any anti-FAS antibody. Anti-FAS antibodies are commercially available, for example, from Cell Signalling Technologies, Inc., Santa Cruz Biotechnology, EMD Biosciences, and others. The detection antibody also may be an anti-FAS antibody as disclosed herein that is specific for one or more of SEQ ID NOs. 1-5. In one embodiment, the detection antibody may be directly conjugated with a detectable label, or an enzyme. If the detection antibody is not conjugated with a detectable label or an enzyme, then a labeled secondary antibody that specifically binds to the detection antibody is included. Such detection antibody "pairs" are commercially available, for example, from Cell Signaling Technologies, Inc.

Techniques for labeling antibodies with detectable labels are well-established in the art. As used herein, the term "detectable label" refers to a composition detectable by spectroscopic, photochemical, biochemical, immunochemical, or chemical means. The detectable label can be selected, e.g., from a group consisting of radioisotopes, fluorescent compounds, chemiluminescent compounds, enzymes, and enzyme co-factors, or any other labels known in the art. See, e.g., Zola, Monoclonal Antibodies: A Manual of Techniques, pp. 147-158 (CRC Press, Inc. 1987). A detectable label can be attached to the subject antibodies and is selected so as to meet the needs of various uses of the method which are often dictated by the availability of assay equipment and compatible immunoassay procedures. Appropriate labels include, without limitation, radionuclides, enzymes (e.g., alkaline phosphatase, horseradish peroxidase, luciferase, or $\beta$-galactosidase), fluorescent moieties or proteins (e.g., fluorescein, rhodamine, phycoerythrin, GFP, or BFP), or luminescent moieties (e.g., Evidot® quantum dots supplied by Evident Technologies, Troy, N.Y., or Qdot™ nanoparticles supplied by the Quantum Dot Corporation, Palo Alto, Calif.).

Preferably, the sandwich immunoassay of the present invention comprises the step of measuring the labeled secondary antibody, which is bound to the detection antibody, after formation of the capture antibody-antigen-detection antibody complex on the solid phase. The method of measuring the labeling substance can be appropriately selected depending on the type of the labeling substance. For example, when the labeling substance is a radioisotope, a method of measuring radioactivity by using a conventionally known apparatus such as a scintillation counter can be used. When the labeling substance is a fluorescent substance, a method of measuring fluorescence by using a conventionally known apparatus such as a luminometer can be used.

When the labeling substance is an enzyme, a method of measuring luminescence or coloration by reacting an enzyme substrate with the enzyme can be used. The substrate that can be used for the enzyme includes a conventionally known luminescent substrate, calorimetric substrate, or the like. When an alkaline phosphatase is used as the enzyme, its substrate includes chemilumigenic substrates such as CDP-star® (4-chloro-3-(methoxyspiro(1,2-dioxetane-3,2'-(5'-chloro)tricyclo[3.3.1.1.-sup.3.7]decane)-4-yl)disodium phenylphosphate) and CSPD® (3-(4-methoxyspiro(1,2-dioxetane-3,2-(5'-chloro)tricyclo[3.3.1.1.sup.3.7]-decane)-4-yl)disodium phenylphosphate) and colorimetric substrates such as p-nitrophenyl phosphate, 5-bromo-4-chloro-3-indolyl-phosphoric acid (BCIP), 4-nitro blue tetrazolium chloride (NBT), and iodonitro tetrazolium (INT). These luminescent or calorimetric substrates can be detected by a conventionally known spectrophotometer, luminometer, or the like.

In a currently preferred embodiment, the detectable labels comprise quantum dots (e.g., Evidot® quantum dots supplied by Evident Technologies, Troy, N.Y., or Qdot™ nanoparticles supplied by the Quantum Dot Corporation, Palo Alto, Calif.). Techniques for labeling proteins, including antibodies, with quantum dots are known. See, e.g., Goldman et al., *Phys. Stat. Sol.*, 229(1): 407-414 (2002); Zdobnova et al., *J. Biomed. Opt.*, 14(2):021004 (2009); Lao et al., *JACS*, 128(46):14756-14757 (2006); Mattoussi et al., *JACS*, 122(49):12142-12150 (2000); and Mason et al., Methods in Molecular Biology: NanoBiotechnology Protocols, 303:35-50 (Springer Protocols, 2005). Quantum-dot antibody labeling kits are commercially available, e.g., from Invitrogen (Carlsbad, Calif.) and Millipore (Billerica, Mass.).

The sandwich immunoassay of the present invention may comprise one or more washing steps. By washing, the unreacted reagents can be removed. For example, when the solid phase comprises a strip of microtiter wells, a washing substance or buffer is contacted with the wells after each step. Examples of the washing substance that can be used include 2-[N-morpholino]ethanesulfonate buffer (MES), or phosphate buffered saline (PBS), etc. The pH of the buffer is preferably from about pH 6.0 to about pH 10.0. The buffer may contain a detergent or surfactant, such as Tween 20.

The sandwich immunoassay can be carried out under typical conditions for immunoassays. The typical conditions for immunoassays comprise those conditions under which the pH is about 6.0 to 10.0 and the temperature is about 30 to 45° C. The pH can be regulated with a buffer, such as phosphate buffered saline (PBS), a triethanolamine hydrochloride buffer (TEA), a Tris-HCl buffer or the like. The buffer may contain components used in usual immunoassays, such as a surfactant, a preservative and serum proteins. The time of contacting the respective components in each of the respective steps can be suitably established depending on the antigen to be measured, the antibody to be used, and the type of the solid phase or the like.

Kits

The invention further provides kits for performing an immunoassay using the antibodies of the present invention. The kits comprise, at a minimum, one or more of the present antibodies fur use as capture or detection agents for determining the presence and amount of FAS in a biological sample. The kit optionally may include reagents useful in performing the assay, additional antibodies for use in capture/detection of FAS, detection reagents, blocking reagents, or washing reagents. The kits may include instructions for performing an immunoassay using the antibodies and reagents.

Utility

The present invention provides antibodies that are specific for and highly reactive with human FAS. Monoclonal antibodies according to the present invention are particularly useful as capture or detection agents in immunoassays for determining FAS expression. Immunoassays utilizing the present antibodies can be used to determine FAS expression from human tissue, cells or sera.

Immunoassays according to the present invention are especially useful for detecting and/or quantifying FAS expression in prostate cancer. It has been shown that FAS overexpression correlates with recurrence of prostate cancer and/or poor responsiveness to certain cancer therapies. Immunoassays of the present invention can be used in lieu of or in addition to standard PSA tests for determining the likelihood that a patient's prostate cancer will recur, and/or if a patient is likely to benefit from certain therapies, e.g., androgen ablation.

The invention is further illustrated by the following non-limiting examples.

EXAMPLES

Example 1

Preparation of Anti-FAS Monoclonal Antibodies

Four murine monoclonal antibodies were prepared by immunizing SCID mice with synthetic FAS peptides, and establishing hybridomas according to the general procedure described by Iyer et al., *Ind. J. Med. Res.*, 123:651-564 (2006). Each mouse was immunized with one peptide as follows:

| Mouse/Hybridoma | Peptide |
|---|---|
| A | SEQ ID NO. 1 VAQGQWEPSGXAP |
| B | SEQ ID NO. 2 PSGPAPTNXGALE |
| D | SEQ ID NO. 4 EVDPGSAELQKVLQGD |
| E | SEQ ID NO. 5 ELSSKADEASELAC |

Humanized monoclonal antibodies were prepared as described by Carter et al., *Proc. Natl. Acad. Sci. USA*, 89:4285-89 (1992) from monoclonal antibodies A, B, D and E. The humanized monoclonal antibodies (MAbs) are referred to hereinafter as FAS 1, FAS 2, FAS 4 and FAS 5.

| Mouse/Hybridoma | Humanized MAb |
|---|---|
| A | FAS 1 |
| B | FAS 2 |
| D | FAS 4 |
| E | FAS 5 |

FAS 4 humanized monoclonal antibody has been deposited with the American Type Culture Collection, ATCC Designation No. PTA-10801.

Example 2

Reactivity of Anti-FAS HuMAbs

The humanized FAS monoclonal antibodies prepared as described in Example 1 were screened against human sera using an ELISA assay according to the following protocol.

Microwell strips (12 8-well strips, Cell Signalling Technology, Inc.) were brought to room temperature. Wash buffer was prepared by diluting 20× wash buffer (Cell Lysis Buffer, CST#9803, Cell Signalling Technology, Inc.) with purified water to make 1× buffer.

Monoclonal antibodies FAS 1, FAS 2, FAS 4 and FAS 5 (Example 1) were used as capture antibodies. The capture antibodies were immobilized in the microwells as described below.

Preparation of Solutions

Capture Antibody Coating Solution: Antibodies to be used as capture antibodies are combined with 50 mM sodium carbonate (pH 9.6), 20 mM Tris HCl (pH 8.5) or 10 mM PBS (pH 7.2), to a protein concentration of between 1-10 μg/ml.

Blocking Solution: Blocking agent (BSA, FBS, nonfat dry milk, casein, or gelatin) is diluted with buffer to a concentration of approximately 1% for BSA, and approximately 5% (or greater) of FBS, nonfat dry milk, casein, or gelatin. Sodium azide is added to a concentration of approximately 0.05%.

Primary/Secondary Detection Antibody Solution: Primary (and secondary, if appropriate) detection antibodies are diluted in 1× blocking solution (to minimize nonspecific binding) to a concentration of 0.1-1.0 μg/ml.

Wash solution: 0.1M PBS or Tris-buffered saline (pH 7.4) is combined with Tween 20 (0.02%-0.05% v/v).

Coating of Microwell Plates with Capture Antibody

Add 100 μl of capture antibody coating solution to each well of a microwell plate or strip, and incubate for 1 hour at room temperature. Empty plate and tap out residual liquid. Block plate by adding 300 μl of blocking solution to the wells, incubating for 5 minutes, and tapping out residual liquid. The plates are ready to be used.

Preparing Cell Lysates

To prepare the sample, the pooled serum was centrifuged to separate cells, which then were lysed using sonication. The media was removed, and cold PBS was added. The PBS was removed and 0.5 mL of cold 1× Cell Lysis buffer plus 1 mM phenylmethylsulfonyl fluoride (PMSF) was added to each plate (10 cm in diameter) and incubated on ice for 5 minutes. The cells were carefully scraped off the plate, and transferred to an appropriate tube, kept on ice. The tubes of cell lysates were sonicated on ice, then microcentrifuged for 10 minutes at 4° C., after which the supernatant containing the cell lysate was transferred to a new tube. The supernatant is the cell lysate. The cell lysate was stored at −80° C. in single-use aliquots until needed.

Test Procedure

Bring microwell plates coated with capture antibody to room temperature. Add 100 μl of sample diluent (Cell Signalling Technology, Inc.) to a microcentrifuge tube, transfer 100 μl of cell lysate into the tube and vortex for a few seconds. 100 μl of each diluted cell lysate were added to the appropriate well, and sealed with tape. The plates were incubated for 2 hours at 37° C. (Alternatively, the plate may be incubated overnight at 4° C.).

The tape was removed and the plate contents decanted into a receptacle. The plates then were washed 4 times with 1× wash solution, 200 μl each time for each well. For each wash, the residual solution in each well was removed, but the wells were not allowed to become completely dry at any time. 100 μl of a solution containing the detection antibody (Cell Signaling Technology, Inc.) to each well. The plates were sealed with tape and incubated for 1 hour at 37° C.

The wash procedure described above then was repeated. 100 μl of HRP-Linked secondary antibody (red color) to each well. The plates were sealed with tape and incubated for 30 minutes at 37° C.

The wash procedure described above was again repeated. 100 μl of TMB Substrate (Cell Signaling Technology, Inc.) was added to each well. The plates were sealed with tape and incubated for 10 minutes at 37° C. or 30 minutes at 25° C. 100 μl of STOP Solution (Cell Signalling Technology, Inc.) was added to each well, and the plates were shaken gently for a few seconds. The initial color of positive reaction is blue, which changes to yellow upon addition of STOP Solution.

For visual determination, the plates must be read within 30 minutes after adding STOP Solution. For spectrophotometric determination, the absorbance must be read at 450 nm within 30 minutes after adding STOP Solution. For this Example, the absorbance was read using a fluorescence plate reader (Thermo Fisher Scientific, Inc.).

ELISA assays were performed to determine FAS expression in cells derived from the pooled sera of two prostate cancer patients. To prepare the sample, the pooled serum was centrifuged to separate cells, which then were lysed using sonication as described above.

The assay parameters were as follows:
Assay Parameters:

| Step | Reagent | Serial dilution | Dilution buffer | Concentration | Volume/vile | Incubation |
|---|---|---|---|---|---|---|
| Ag coating | FAS 1, 2, 4 or 5 | — | 0.15M PBS | 2 μg/mL | 50 μL | 1 hr @ 37 C. |
| Blocking | SeaBlock* | — | — | NEAT | 300 μL | 30 min. @ 37 C. |
| Sample Dilution | see below | 5X | 0.15M PBS | starting @ 1:50 | 80 μ·L | 30 min. @ R.T. |
| Secondary Ab | anti-Rb HRP** | — | 15M PBS w 0.05% Tween20 | 1:10000 | 50 μ·L | 30 min. @ R.T. |

*Supplied by East Coat Biologics, North Berwick, ME
**Supplied by Cell Signaling Technology, Inc.

Absorbance was measured at 450 nm using a Thermo Shandon plate reader.

The data obtained for the ELISA using FAS 1, 2, 5 and 5 are shown in the tables below. In the tables, the term "pre-purification" refers to the murine monoclonal antibody prior to humanization and affinity purification, and "post-purification" refers to the monoclonal antibody after humanization and affinity purification. Data for pre-purified and post-purified antibodies are included for comparison.

The data for FAS 1 and 2 are shown in Table 2-1:

TABLE 2-1

ELISA Results for FAS 1 and 2
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 1 | 0.03 | 0.02 | 0.014 | 0.01 | 0.01 | 0.01 | 0.008 | 0.005 | 0.01 | 0 | 0.01 | 0 |
| Pre-purification FAS 2 | 0.07 | 0.06 | 0.022 | 0.04 | 0.01 | 0.02 | 0.01 | 0.007 | 0 | 0 | 0.01 | 0.01 |
| Post-purification FAS 1 | 0.67 | 0.02 | 0.766 | 0.02 | 0.96 | 0.01 | 0.598 | 0.18 | 0.176 | 0.01 | 0.05 | 0 |
| Post-purification FAS 2 | 0.59 | 0.02 | 0.659 | 0.03 | 0.78 | 0.02 | 0.439 | 0.12 | 0.12 | 0 | 0.03 | 0.02 |

FIG. 1 shows the data in Table 1 in graphical form. For each dilution, the two left columns represent the pre-purification MAbs, and the two right columns represent the post-purification MAbs. The graph shows that the FAS 1 and 2 antibodies were able to detect significant levels of FAS in the patient sera even at very high dilutions.

The data obtained for the ELISA using FAS 4 are shown in Table 2-2:

TABLE 2-2

ELISA Results for FAS 4
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 4 | 0.03 | 0.02 | 0.014 | 0.01 | 0.01 | 0.01 | 0.008 | 0.005 | 0.01 | 0 | 0.01 | 0 |
| Pre-purification FAS 4a | 0.07 | 0.06 | 0.022 | 0.04 | 0.01 | 0.02 | 0.01 | 0.007 | 0 | 0 | 0.01 | 0.01 |
| Post-purification FAS 4 | 0.67 | 0.02 | 0.766 | 0.02 | 0.96 | 0.01 | 0.598 | 0.007 | 0.18 | 0.01 | 0.05 | 0 |
| Post-purification FAS 4a | 0.59 | 0.02 | 0.659 | 0.03 | 0.78 | 0.02 | 0.439 | 0.009 | 0.12 | 0 | 0.03 | 0.02 |

Figure 2:
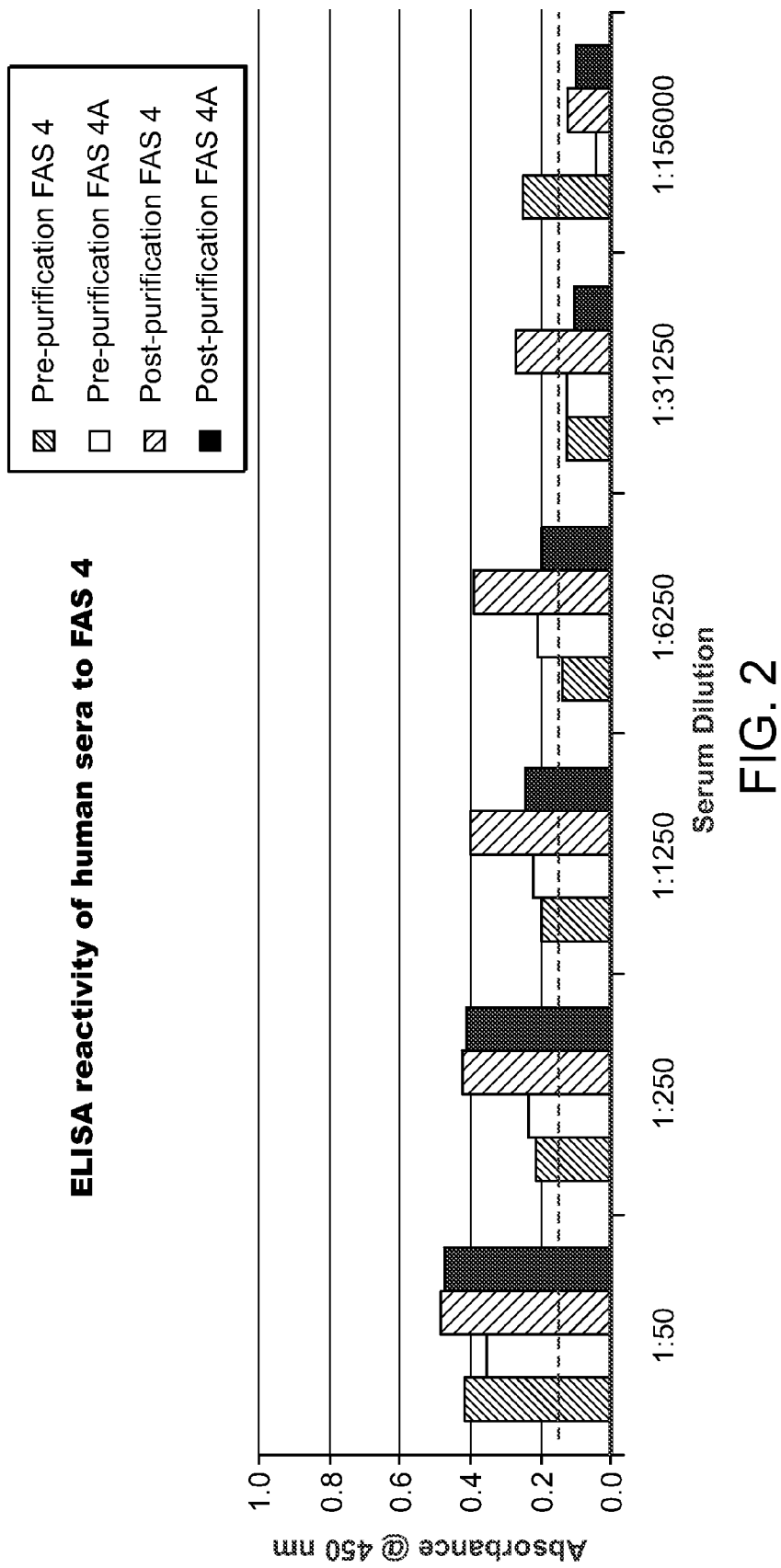
FIG. 2 is a graph showing the results of an ELISA assay using a monoclonal antibody of the present invention raised against the peptide of SEQ. ID NO. 4 as the capture antibody. For each dilution, the two left columns represent the pre-purification MAbs, and the two right columns represent the post-purification MAbs.

FAS 4 and FAS 4a represent two separate batches of FAS 4. FIG. 2 shows the data in graphical form. For each dilution, the two left columns represent the pre-purification MAbs, and the two right columns represent the post-purification MAbs. The graph shows that the FAS 4 antibody was able to detect significant levels of FAS in the patient sera even at very high dilutions.

The data obtained for the ELISA using FAS 5 are shown in Table 2-3:

TABLE 2-3

ELISA Results for FAS 5
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 5 | 0.02 | 0 | 0.02 | 0.01 | 0.03 | 0.02 | 0.01 | 0.013 | 0.02 | 0.01 | 0.02 | 0.02 |
| Pre-purification FAS 5a | 0 | 0.02 | 0.03 | 0.02 | 0.05 | 0.02 | 0.02 | 0 | 0.01 | 0.01 | 0.03 | 0.09 |
| Post-purification FAS 5 | 0.59 | 0.06 | 1.434 | 0.08 | 1.15 | 0.04 | 1.484 | −0.15 | 1.07 | 0.03 | 0.27 | 0.01 |
| Post-purification FAS 5a | 0.46 | 0.3 | 0.441 | 0.01 | 0.41 | 0 | 0.234 | 0.018 | 0.09 | 0.02 | 0.09 | 0.08 |

Figure 3:
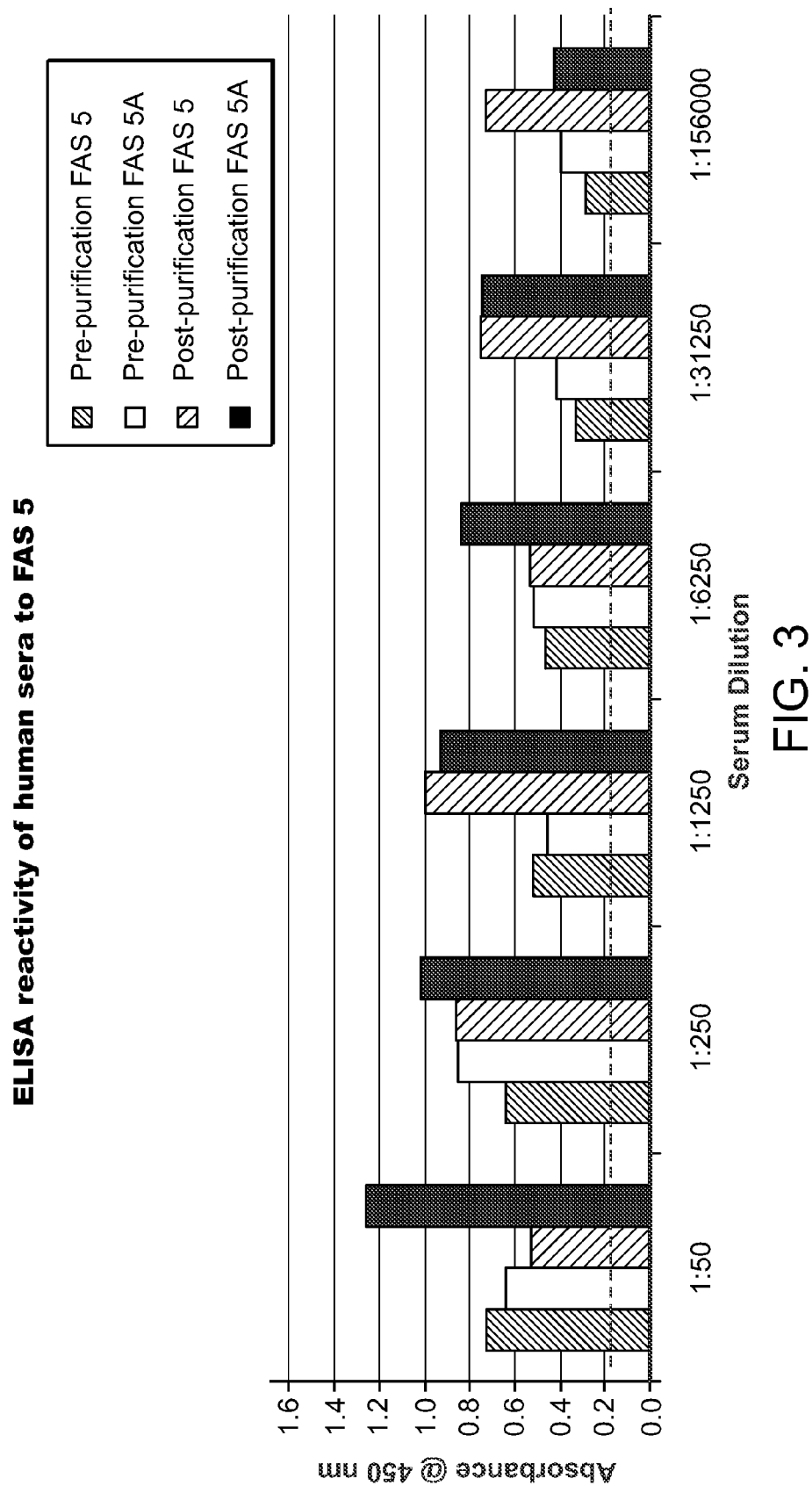
FIG. 3 is a graph showing the results of an ELISA assay using a monoclonal antibody of the present invention raised against the peptide of SEQ. ID NO. 5 as the capture antibody. For each dilution, the two left columns represent the pre-purification MAbs, and the two right columns represent the post-purification MAbs.
Figure 4:
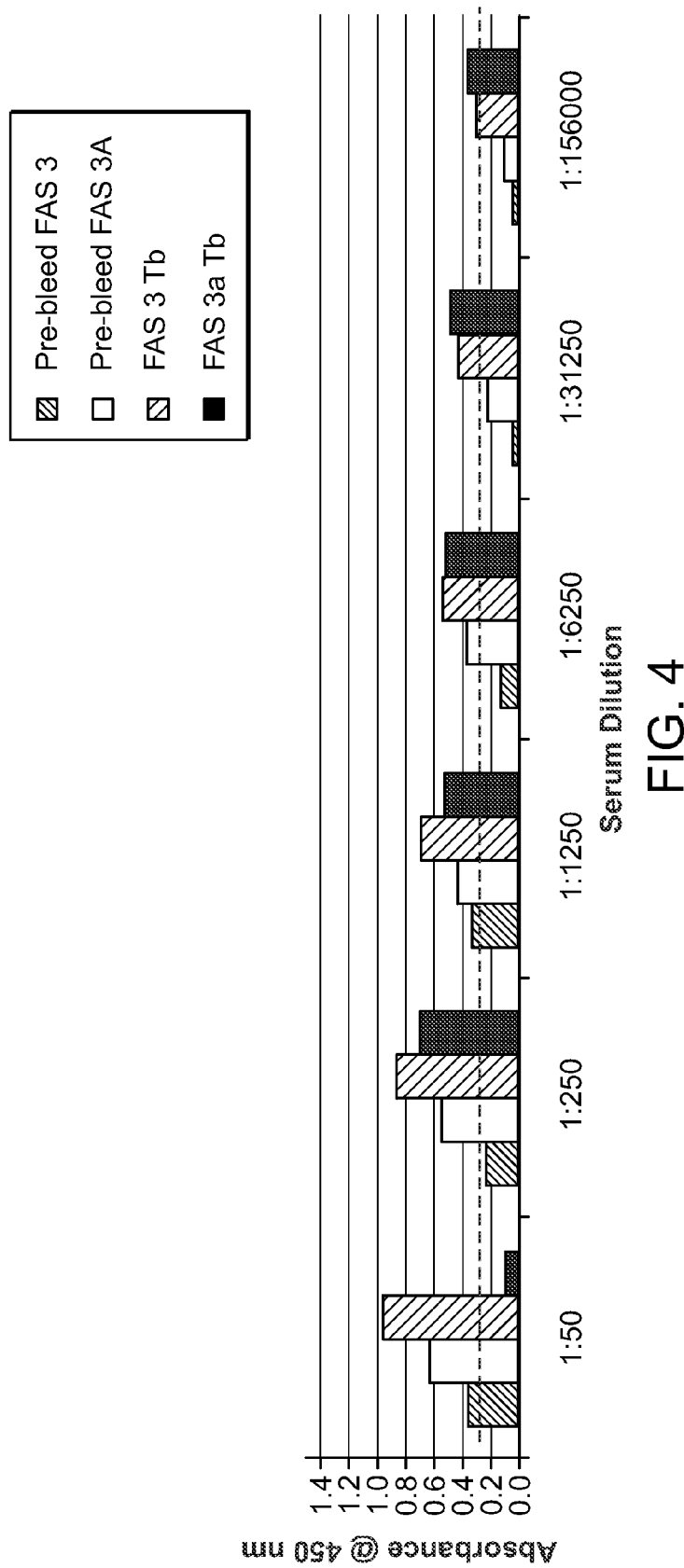
FIG. 4 is a graph showing the results of an ELISA assay using polyclonal antisera of the present invention raised against the peptide of SEQ. ID NO. 3 as the capture antibody. For each dilution, the two left columns represent the pre-purification MAbs, and the two right columns represent the post-purification MAbs.

FAS 5 and FAS 5a represent two separate batches of FAS 5. FIG. 3 shows the data in graphical form. For each dilution, the two left columns represent the pre-purification MAbs, and the two right columns represent the post-purification MAbs. The graph shows that the FAS 5 antibody was able to detect significant levels of FAS in the patient sera even at very high dilutions.

Example 3

Comparison of FAS and PSA as Prognostic Indicators in Prostate Cancer

Biopsy specimens from ninety patients diagnosed with prostate cancer (PCa) were prepared and analyzed as described below. All patients had been treated by androgen ablation.

Tissue microarrays (TMAs) were prepared as described in US 2008/0206777 A1. In addition to the 90 prostate cancer specimens, TMAs containing normal prostate tissue, benign prostatic hyperplasia (BPH) and normal (non-cancerous) tissues were prepared and analyzed.

TABLE A

| Tissue Micro Arrays | |
|---|---|
| Prostate Cancer Progression Array | This array contained the patient samples obtained from patients afflicted with recurrent/metastatic and non-recurrent prostate cancer. The characteristics of these 90 samples are shown in Table C. |
| Normal Prostate/ BPH Screening Array | This array contained samples of normal (non-cancerous) prostate tissue, and benign prostatic hyperplasia (BPH) tissue. This array was included as a negative control to confirm that FAS overexpression does not occur in non-cancerous prostate tissue. |
| Test Array | This array contained samples of the following normal |
| (TE-30 Array) | (non-cancerous) tissues: colon, liver, lung, prostate and breast. This array is included for antibody dilution and as a negative control to confirm that FAS overexpression does not occur in any of these normal tissues. |

TABLE B

The 90 prostate cancer samples had the following characteristics:

| Primary Tumor Stage | Number of Patients | Number of Patients with Recurrence of PCa |
|---|---|---|
| 2a | 13 | 2 |
| 2b | 4 | 2 |
| 2c | 27 | 9 |
| 3a | 25 | 8 |
| 3b | 19 | 11 |
| 3c | 0 | 0 |
| 4 | 2 | 2 |
| Total | 90 | 34 |

FAS expression was determined by immunohistochemistry (IHC) according to the method described in US 2008/0206777 A1, using MAb D (Example 1) as the detection (primary) antibody. The detection antibody was visualized using a biotinylated link antibody and streptavidin-HRP as described in US 2008/0206777 A1. The results for the 90 prostate cancer samples are shown in Table C below; in Table C, FAS overexpression (at least 2-fold compared to expression levels in normal tissue or cells) is indicated by a + sign.

The results for the TE-30 array and the Normal Prostate/BPH Screening Array were negative for FAS expression.

TABLE C

Clinical and pathological data on 90 cases of treated (androgen ablated) prostate cancer

| Patient No. | Age (years) | Biopsy Gleason score | Pre-therapy PSA (ng/ml) | FAS | Months of therapy | Degree of regression (3 grade system) | TNM 2002 |
|---|---|---|---|---|---|---|---|
| 1 | 69 | 3 + 4 = 7 | 8.7 | + | 3 | Poor | pT3aN0R0 |
| 2 | 70 | 3 + 3 = 6 | 7.0 | + | 1 | Poor | pT3aNXR0 |
| 3 | 72 | 2 + 3 = 5 | 21.0 | − | 6 | Excellent | pT2cN0R0 |
| 4 | 68 | 2 + 2 = 4 | 14.0 | + | 7 | Poor | pT2cNXR0 |
| 5 | 60 | 2 + 3 = 5 | 24.0 | − | 3 | Good | pT2cNXR0 |
| 6 | 68 | 3 + 3 = 6 | + | + | 3 | Poor | pT3bN0R1 |
| 7 | 58 | 3 + 3 = 6 | 10.2 | + | 3 | Poor | pT3a NXR1 |

TABLE C-continued

Clinical and pathological data on 90 cases of treated (androgen ablated) prostate cancer

| Patient No. | Age (years) | Biopsy Gleason score | Pre-therapy PSA (ng/ml) | FAS | Months of therapy | Degree of regression (3 grade system) | TNM 2002 |
|---|---|---|---|---|---|---|---|
| 8 | 57 | 3 + 3 = 6 | 9.8 | + | 3 | Poor | pT3aNXR0 |
| 9 | 70 | 3 + 3 = 6 | 5.2 | + | 2 | Poor | pT2cN0R1 |
| 10 | 64 | 3 + 3 = 6 | 2.6 | − | 3 | Good | pT2cNXR1 |
| 11 | 65 | 3 + 3 = 6 | 5.0 | + | 5 | Poor | pT3aN0R0 |
| 12 | 66 | 4 + 3 = 7 | 6.0 | + | 5 | Poor | pT3aN0R1 |
| 13 | 61 | 3 + 3 = 6 | 7.6 | − | 6 | Good | pT3aN0R0 |
| 14 | 68 | 3 + 4 = 7 | 9.7 | − | 3 | Good | pT2cN0R1 |
| 15 | 67 | 3 + 3 = 6 | 9.4 | + | 6 | Poor | pT3bN0R0 |
| 16 | 57 | 2 + 3 = 5 | 19.0 | + | 2 | Good | pT2cN0R0 |
| 17 | 67 | 3 + 3 = 6 | 9.5 | + | 7 | Poor | pT3bN1R0 |
| 18 | 57 | 3 + 4 = 7 | 34.0 | + | 4 | Poor | pT3bNXR1 |
| 19 | 58 | 3 + 3 = 6 | 18.0 | − | 11 | Excellent | pT3aN0R0 |
| 20 | 72 | 3 + 3 = 6 | 6.5 | + | 2 | Poor | pT3a N0R0 |
| 21 | 70 | 3 + 3 = 6 | 8.7 | + | 3 | Poor | pT3a N0R1 |
| 22 | 65 | 4 + 3 = 7 | 16.3 | + | 5 | Poor | pT2cN0R1 |
| 23 | 68 | 3 + 4 = 7 | 41.7 | − | 6 | Excellent | pT4N0R1 |
| 24 | 62 | 3 + 3 = 6 | 13.0 | + | 3 | Poor | pT3a N0R0 |
| 25 | 64 | 2 + 3 = 5 | 2.4 | + | 1 | Poor | pT2bN0R0 |
| 26 | 78 | 3 + 4 = 7 | 13.4 | − | 2 | Excellent | pT2c N0R0 |
| 27 | 56 | 3 + 4 = 7 | 17.1 | − | 24 | Good | pT3b N0R1 |
| 28 | 65 | 3 + 3 = 6 | 16.0 | + | 4 | Poor | pT3b N0R0 |
| 29 | 72 | 3 + 3 = 6 | 19.0 | + | 2 | Poor | pT3a N0R0 |
| 30 | 68 | 3 + 5 = 8 | 2.15 | + | 1 | Poor | pT3a N0R0 |
| 31 | 66 | 4 + 3 = 7 | 12.0 | + | 12 | Poor | pT3b N1R0 |
| 32 | 65 | 3 + 3 = 6 | 2.4 | + | 4 | Poor | pT3b N0R1 |
| 33 | 69 | 3 + 3 = 6 | 7.0 | + | 1 | Poor | pT2a NXR0 |
| 34 | 68 | 3 + 3 = 6 | 17.5 | − | 5 | Good | pT2c N0R1 |
| 35 | 67 | 3 + 4 = 7 | 7.3 | + | 6 | Poor | pT3a NXR1 |
| 36 | 53 | 2 + 2 = 4 | 3.7 | − | 3 | Good | pT2c N0R0 |
| 37 | 66 | 3 + 3 = 6 | 10.6 | − | 2 | Poor | pT2c N0R0 |
| 38 | 74 | 3 + 3 = 6 | 15.9 | − | 2 | Poor | pT2c N0R0 |
| 39 | 69 | 4 + 4 = 8 | 31.0 | − | 6 | Good | pT2cN0R0 |
| 40 | 70 | 3 + 3 = 6 | 7.3 | + | 3 | Poor | pT3b N0R1 |
| 41 | 59 | 4 + 4 = 8 | 27.0 | + | 2 | Poor | pT3a N0R0 |
| 42 | 67 | 3 + 4 = 7 | 16.5 | + | 1 | Poor | PT2c NXR0 |
| 43 | 62 | 3 + 3 = 6 | 5.4 | − | 2 | Good | pT3a NXR1 |
| 44 | 69 | 4 + 4 = 8 | 8.2 | + | 5 | Poor | PT2c N0R1 |
| 45 | 73 | 3 + 3 = 6 | 1.8 | + | 2 | Poor | pT3a NXR0 |
| 46 | 59 | 3 + 4 = 7 | 9.3 | + | 6 | Poor | pT2a N0R0 |
| 47 | 69 | 3 + 3 = 6 | 12.6 | + | 3 | Poor | pT2c N0R0 |
| 48 | 66 | 4 + 3 = 7 | 13.5 | + | 6 | Poor | pT2a N0R0 |
| 49 | 50 | 4 + 3 = 7 | 101.0 | + | 4 | Poor | pT4 N1R1 |
| 50 | 53 | 3 + 3 = 6 | 10.0 | + | 1 | Poor | pT2a N0R1 |
| 51 | 70 | 4 + 4 = 8 | 10.9 | + | 3 | Poor | pT2a N0R0 |
| 52 | 55 | 3 + 3 = 6 | 9.7 | + | 4 | Good | pT2c N0R0 |
| 53 | 61 | 3 + 3 = 6 | 6.4 | + | 3 | Poor | pT3b N1R1 |
| 54 | 74 | 3 + 3 = 6 | 28.0 | − | 6 | Excellent | pT3b N0R0 |
| 55 | 71 | 3 + 4 = 7 | 8.3 | + | 3 | Good | pT3a N0R0 |
| 56 | 71 | 3 + 3 = 6 | 17.0 | + | 1 | Poor | pT2c N0R1 |
| 57 | 67 | 3 + 3 = 6 | 2.0 | − | 5 | Excellent | pT2a N0R0 |
| 58 | 62 | 3 + 3 = 6 | 16.6 | − | 3 | Good | pT2c N0R0 |
| 59 | 69 | 3 + 3 = 6 | 6.31 | + | 1 | Poor | pT2c NXR0 |
| 60 | 72 | 3 + 3 = 6 | 11.8 | + | 2 | Poor | pT2c N0R0 |
| 61 | 65 | 3 + 3 = 6 | 5.2 | + | 2 | Poor | pT2c N0R0 |
| 62 | 66 | 3 + 4 = 7 | 7.4 | + | 1 | Poor | pT3b N0R1 |
| 63 | 66 | 4 + 3 = 7 | 13.5 | − | 3 | Good | pT3b N0R0 |
| 64 | 74 | 3 + 3 = 6 | 12.8 | − | 4 | Excellent | pT2a NXR0 |
| 65 | 66 | 3 + 3 = 6 | 9.8 | + | 2 | Poor | pT3b N0R0 |
| 66 | 66 | 3 + 3 = 6 | 8.1 | − | 2 | Good | pT2c NXR1 |
| 67 | 64 | 3 + 3 = 6 | 1.7 | − | 7 | Excellent | pT2a NXR0 |
| 68 | 69 | 3 + 4 = 7 | 5.0 | − | 3 | Good | pT2c N0R0 |
| 69 | 54 | 3 + 3 = 6 | 11.8 | + | 3 | Poor | PT3b NXR1 |
| 70 | 69 | 3 + 3 = 6 | 6.2 | + | 3 | Good | PT3a N0R0 |
| 71 | 63 | 3 + 4 = 7 | 8.6 | + | 3 | Good | pT2c NXR0 |
| 72 | 59 | 3 + 4 = 7 | 12.2 | + | 3 | Poor | pT2a N0R1 |
| 73 | 65 | 4 + 3 = 7 | 4.8 | + | 2 | Good | pT2a N0R0 |
| 74 | 64 | 3 + 3 = 6 | 7.6 | + | 1 | Poor | pT2a N0R0 |
| 75 | 72 | 3 + 3 = 6 | 8.4 | + | 2 | Poor | pT2c N0R1 |
| 76 | 68 | 3 + 4 = 7 | 7.8 | + | 3 | Poor | pT2b N1R0 |
| 77 | 65 | 3 + 3 = 6 | 24.0 | + | 5 | Good | pT2b N0R0 |
| 78 | 65 | 3 + 3 = 6 | 6.4 | + | 6 | Poor | pT3a NXR0 |
| 79 | 71 | 3 + 4 = 7 | 9.6 | − | 2 | Poor | pT3a N0R1 |
| 80 | 62 | 4 + 5 = 9 | 27.0 | − | 4 | Excellent | pT2a N0R0 |
| 81 | 71 | 3 + 3 = 6 | 11.6 | + | 3 | Good | pT2a N0R0 |
| 82 | 67 | 4 + 3 = 7 | 25.0 | + | 1 | Poor | pT3b NXR1 |

TABLE C-continued

Clinical and pathological data on 90 cases of treated (androgen ablated) prostate cancer

| Patient No. | Age (years) | Biopsy Gleason score | Pre-therapy PSA (ng/ml) | FAS | Months of therapy | Degree of regression (3 grade system) | TNM 2002 |
|---|---|---|---|---|---|---|---|
| 83 | 67 | 3 + 3 = 6 | 22.9 | + | 9 | Poor | pT3b N1R1 |
| 84 | 72 | 3 + 4 = 7 | 7.4 | − | 3 | Excellent | pT2b N0R0 |
| 85 | 71 | 4 + 3 = 7 | 1.3 | − | 4 | Excellent | PT3b N0R1 |
| 86 | 69 | 4 + 3 = 7 | 4.8 | + | 3 | Poor | pT3a N0R1 |
| 87 | 68 | 4 + 3 = 7 | 9.0 | + | 1 | Poor | pT3b N0R0 |
| 88 | 70 | 3 + 3 = 6 | 6.1 | − | 3 | Good | pT3a N0R0 |
| 89 | 71 | 4 + 3 = 7 | 20.4 | + | 1 | Poor | pT3a N0R0 |
| 90 | 65 | 3 + 3 = 6 | 5.8 | + | 3 | Poor | pT3a NXR1 |

The results in Table C show that:

Significant FAS overexpression (e.g., 2-fold or higher) was detected in 62 of the patient biopsy samples;

FAS overexpression correlates with recurrence of Pca and/or poor responsiveness to androgen ablation therapy in all but 8 of these patients (a positive correlation of 87%);

In patients not exhibiting FAS overexpression (28 patients), the lack of FAS overexpression correlated with good or excellent tumor regression after treatment with androgen ablation in all but three patients (a positive correlation of 89%).

However, the correlation between the absence of FAS overexpression and recurrence of PCa was lower: 9 patients out of 28 (32%) whose tumors showed no FAS overexpression experienced recurrence of their cancer.

In contrast, PSA was a much poorer prognostic indicator. Of the 90 patients in the study, 39 had pre-therapy PSA levels above 10 ng/ml. Of these, only 17 evidenced good or excellent tumor regression after androgen ablation therapy (a positive correlation of only 44%). PSA levels also showed a low correlation with recurrence: of the 39 patients having a pre-therapy PSA levels above 10 ng/ml, only 12 experienced tumor recurrence (a positive correlation of about 31%).

The pathological samples and clinical data for the patients listed in Table C were further analyzed using the Applied Imaging Ariol® platform (Genetix Corp., San Jose, Calif.) as well as the TMAJ software (Johns Hopkins University TMA Core Facility, Baltimore, Md.). The data analyzed included the PSA serum levels, FAS expression levels, recurrence of cancer, metastasis of cancer, and the length of time until recurrence or metastasis. The results showed a strong correlation between FAS expression and recurrence: patients whose disease is characterized by a high level of FAS expression experienced higher levels of recurrence and shorter times until recurrence of their disease. The results are summarized below:

Correlation of FAS Expression with Recurrence

| Univariate Analysis | | Multivariate Analysis | |
|---|---|---|---|
| Hazard Ratio (95% CI) | P-value | Hazard Ratio (95% CI) | P-value |
| 1.69 (1.41-2.04) | <0.0001 | 1.48 (1.21-1.80) | 0.0001 |

In contrast, the same analysis showed a poor correlation between PSA levels and recurrence of disease. In many cases, the presence of high levels of PSA was not predictive of recurrence of a patient's disease.

The results further showed a strong correlation between FAS expression and metastasis: patients whose disease is characterized by a high level of FAS expression experienced higher levels of metastasis and shorter times until metastasis of their disease. These results are summarized below:

Correlation of FAS Expression with Metastasis

| Univariate Analysis | |
|---|---|
| Hazard Ratio (95% CI) | P-value |
| 1.32 (1.04-1.68) | 0.02 |

The results of this study indicate that FAS expression is a promising prognostic indicator for prostate cancer.

Example 4

ELISA Assay for FAS Expression in DU-145 PCa Cells

Microwell strips (12 8-well strips, Cell Signalling Technology, Inc.) were brought to room temperature. Wash buffer was prepared by diluting 20× wash buffer (Cell Lysis Buffer, CST#9803, Cell Signalling Technology, Inc.) with purified water to make 1× buffer.

Two monoclonal antibodies (MAbs D and E, Example 1) were used as capture antibodies. The capture antibodies were immobilized in the microwells according to the following procedure:

Preparation of Solutions

Capture Antibody Coating Solution: Antibodies to be used as capture antibodies are combined with 50 mM sodium carbonate (pH 9.6), 20 mM Tris HCl (pH 8.5) or 10 mM PBS (pH 7.2), to a protein concentration of between 1-10 µg/ml.

Blocking Solution: Blocking agent (BSA, FBS, nonfat dry milk, casein, or gelatin) is diluted with buffer to a concentration of approximately 1% for BSA, and approximately 5% (or greater) of FBS, nonfat dry milk, casein, or gelatin. Sodium azide is added to a concentration of approximately 0.05%.

Primary/Secondary Detection Antibody Solution: Primary (and secondary, if appropriate) detection antibodies are diluted in 1× blocking solution (to minimize nonspecific binding) to a concentration of 0.1-1.0 µg/ml.

Wash solution: 0.1M PBS or Tris-buffered saline (pH 7.4) is combined with Tween 20 (0.02%-0.05% v/v).

Coating of Microwell Plates with Capture Antibody

Add 100 µl of capture antibody coating solution to each well of a microwell plate or strip, and incubate for 1 hour at room temperature. Empty plate and tap out residual liquid. Block plate by adding 300 µl of blocking solution to the wells, incubating for 5 minutes, and tapping out residual liquid. The plates are ready to be used.

Preparing Cell Lysates

The media was aspirated from cultures of DU-145 prostate cancer cells (obtained from the National Cancer Institute), and fresh media was added. The cells were harvested under non-denaturing conditions according to the following protocol. The media was removed, and cold PBS was added. The PBS was removed and 0.5 mL of cold 1× Cell Lysis buffer plus 1 mM phenylmethylsulfonyl fluoride (PMSF) was added to each plate (10 cm in diameter) and incubated on ice for 5 minutes. The cells were carefully scraped off the plate, and transferred to an appropriate tube, kept on ice. The tubes of cell lysates were sonicated on ice, then microcentrifuge d for 10 minutes at 4° C., after which the supernatant containing the cell lysate was transferred to a new tube. The supernatant is the cell lysate. The cell lysate was stored at −80° C. in single-use aliquots until needed.

Test Procedure

Bring microwell plates coated with capture antibody to room temperature. Add 100 µA of sample diluent (Cell Signalling Technology, Inc.) to a microcentrifuge tube, transfer 100 µl of cell lysate into the tube and vortex for a few seconds. 100 µl of each diluted cell lysate were added to the appropriate well, and sealed with tape. The plates were incubated for 2 hours at 37° C. (Alternatively, the plate may be incubated overnight at 4° C.).

The tape was removed and the plate contents decanted into a receptacle. The plates then were washed 4 times with 1× wash solution, 200 µl each time for each well. For each wash, the residual solution in each well was removed, but the wells were not allowed to become completely dry at any time. 100 µl of a solution containing the detection antibody (Cell Signaling Technology, Inc.) to each well. The plates were sealed with tape and incubated for 1 hour at 37° C.

The wash procedure described above then was repeated. 100 µl of HRP-Linked secondary antibody (red color) to each well. The plates were sealed with tape and incubated for 30 minutes at 37° C.

The wash procedure described above was again repeated. 100 µl of TMB Substrate (Cell Signaling Technology, Inc.) was added to each well. The plates were sealed with tape and incubated for 10 minutes at 37° C. or 30 minutes at 25° C. 100 µl of STOP Solution (Cell Signalling Technology, Inc.) was added to each well, and the plates were shaken gently for a few seconds. The initial color of positive reaction is blue, which changes to yellow upon addition of STOP Solution.

Results

For visual determination, the plates must be read within 30 minutes after adding STOP Solution. For spectrophotometric determination, the absorbance must be read at 450 nm within 30 minutes after adding STOP Solution. For this Example, the absorbance was read using a fluorescence plate reader (Thermo Fisher Scientific, Inc.).

Significant levels of FAS expression were observed from the cells, indicating that the assay is effective.

Example 5

ELISA Assay for FAS Expression in Sera from PCa Patients

ELISA assays were performed to determine FAS expression in cells derived from the sera of two prostate cancer patients (Patients 30 and 87 from Table C). To prepare the sample, the sera were centrifuged to separate cells, which then were lysed using sonication.

Anti-FAS MAbs D and E were used as capture antibodies. In addition, two rabbits (New Zealand White Rabbits, Maine Biotechnology Services, Inc.) were injected with peptides D and E (SEQ. ID. NOs. 4 and 5), and antisera from the rabbits were used to titrate the MAbs. The assay was performed according to the procedure set forth in Example 4; the assay parameters were as follows:

Assay parameters:

| Step | Reagent | Serial dilution | Dilution buffer | Concentration | Vol/well | Incubation |
|---|---|---|---|---|---|---|
| Ab coating | MAb D or E | — | 0.15M PBS | 2 µg/ml | 50 µl | 1 hr@37° C. |
| Blocking | Sea Block* | — | — | NEAT | 300 µl | 30 min@37° C. |
| Sample dilution | 1:50- 1:156000 | 5X | 0.15M PBS | Starting at 1:50 | 80 µl | 30 min@RT |
| Secondary (detection) Ab | Anti-Rb HRP** | — | 0.15M PBS w/0.05% Tween20 | 1:10000 | 50 µl | 30 min@RT |

*Supplied by East Coat Biologics, North Berwick, ME
**Supplied by Cell Signaling Technology, Inc.

Absorbance was measured at 450 nm using a Thermo Shandon plate reader. MAb D is referred to in the charts below as "FAS 4" and MAb E is referred to as "FAS 5."

The data obtained for the ELISA using MAb D are shown in Table 5-1:

TABLE 5-1

Results for FAS 4 ELISA

Dilution:

| | 1:50 | 1:250 | 1:1250 | 1:6250 | 1:31250 | 1:156000 |
|---|---|---|---|---|---|---|
| Pre-bleed Rb 1 | 0.100 | −0.048 | −0.030 | −0.430 | −0.040 | −0.001 |
| Pre-bleed Rb 2 | 0.000 | 0.006 | −0.010 | −0.006 | −0.900 | −0.007 |
| FAS1 | 1.000 | 1.250 | 1.310 | 1.010 | 0.221 | 0.168 |
| FAS1 | 0.040 | 0.790 | 0.380 | 0.329 | 0.613 | 0.145 |
| Pre-bleed Rb 1 | 0.100 | 0.000 | 0.000 | 0.000 | 0.000 | 0.000 |
| Pre-bleed Rb 2 | 0.000 | 0.006 | 0.000 | 0.000 | 0.000 | 0.000 |

TABLE 5-1-continued

Results for FAS 4 ELISA

| | Dilution: | | | | |
|---|---|---|---|---|---|
| 1:50 | 1:250 | 1:1250 | 1:6250 | 1:31250 | 1:156000 |

| | 1:50 | 1:250 | 1:1250 | 1:6250 | 1:31250 | 1:156000 |
|---|---|---|---|---|---|---|
| FAS1 | 1.000 | 1.250 | 1.310 | 1.010 | 0.221 | 0.168 |
| FAS1 | 0.040 | 0.790 | 0.380 | 0.329 | 0.613 | 0.145 |

Reliable absorbance readings could not be obtained for the rabbit antisera under these conditions; it is believed that that concentration of fluorescent label was too dense, thereby masking the signal. The results show that the assay was able to detect significant levels of FAS in the patient sera even at very high dilutions.

The data obtained for the ELISA using MAb E are shown in Table 5-2:

TABLE 5-2

Results for FAS 5 ELISA

| | 1:50 | 1:250 | 1:1250 | 1:6250 | 1:31250 | 1:156000 |
|---|---|---|---|---|---|---|
| Pre-bleed Rb 1 | 0.360 | 0.660 | 0.156 | −0.003 | 0.960 | −0.001 |
| Pre-bleed Rb 2 | −0.022 | 0.006 | 0.031 | 0.020 | 0.001 | −0.064 |
| FAS2 | 0.786 | 1.356 | 1.113 | 1.631 | 1.033 | 0.258 |
| FAS2 | 0.690 | 0.580 | 0.850 | 0.630 | 0.950 | 0.530 |
| Pre-bleed Rb 1 | 0.330 | 0.869 | 0.523 | 0.330 | 0.200 | 1.200 |
| Pre-bleed b 2 | 0.000 | 0.006 | 0.031 | 0.020 | 0.001 | 0.123 |
| FAS2 | 0.786 | 1.960 | 1.520 | 1.520 | 1.430 | 1.630 |
| FAS2 | 0.870 | 0.580 | 0.850 | 0.630 | 0.950 | 0.530 |

As with the FAS1 antibody, reliable absorbance readings could not be obtained for the rabbit antisera under these conditions. The results show that the assay was able to detect significant levels of FAS in the patient sera even at very high dilutions.

These data indicate that the MAbs are highly reactive, resulting in a sensitive and accurate assay for the presence of FAS in circulating cells obtained from patient sera.

REFERENCES

1. Chirala et al., *Proc. Natl. Acad. Sci. USA*, (May 27, 1997) 94(11):5588-93.
2. Kuhajda et al., *Proc. Natl. Acad. Sci. USA*, (Mar. 28, 2000) 97(7):3450-4.
3. Rossi et al., *Mol. Cancer. Res.*, (August 2003), 1(10):707-15.
4. Visca et al., *Anticancer Res.*, (November-December 2004), 24(6):4169-73.
5. Takahiro et al., *Clin. Cancer Res.*, (June 2003), 9(6):2204-12
6. Shurbaji et al., *Hum. Pathol.*, (September 1996), 27(9): 917-21.
7. Alo et al, *Cancer*, (February 1996), 77(3):474-82.
8. Baron et al., *J. Cell Biochem.*, (January 2004), 19(1):47-53.
9. Thompson et al., CA (May 2004), *N Engl. J. Med.*, 350 (22): 2239-46.
10. Carter H B (May 2004), *N. Engl. J. Med.*, 350 (22): 2292-4.
11. Herschman et al., (August 1997), *Urology*, 50 (2): 239-43.
12. Nadler et al., (August 1995), *J. Urol.*, 154 (2 Pt 1): 407-13.
13. Catalona et al., (1997), *JAMA*, 277 (18): 1452-5.

What is claimed is:

1. A method for monitoring the progression of cancer, comprising the steps of:
   i. contacting a biological sample from a cancer patient with a first purified anti-FAS antibody that is specific for the peptide encoded by SEQ ID NO 5, under conditions sufficient to form a conjugate of the antibody and FAS protein in the sample;
   ii. contacting the conjugate formed in step (a) with a second anti-FAS antibody, wherein the second antibody is tagged with a detectable label;
   iii. determining the amount of FAS protein present in the sample; and
   iv. correlating the amount of FAS present in the sample with aggressiveness of the cancer;
   wherein the presence of a high level of FAS in the sample is indicative of an aggressive form of the cancer.

2. The method of claim 1, wherein the biological sample is serum.

3. The method of claim 1, wherein the detectable labels are fluorescent labels.

4. The method of claim 1, wherein the first antibody is disposed on a substrate.

5. The method of claim 4, wherein the substrate is a microtiter plate.

* * * * *

SEQUENCE LISTING

```
<160> NUMBER OF SEQ ID NOS: 5

<210> SEQ ID NO 1
<211> LENGTH: 13
<212> TYPE: PRT
<213> ORGANISM: Human
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Val Ala Gln Gly Gln Trp Glu Pro Ser Gly Xaa Ala Pro
1               5                   10

<210> SEQ ID NO 2
<211> LENGTH: 13
<212> TYPE: PRT
<213> ORGANISM: Human
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Pro Ser Gly Pro Ala Pro Thr Asn Xaa Gly Ala Leu Glu
1               5                   10
```

```
<210> SEQ ID NO 3
<211> LENGTH: 13
<212> TYPE: PRT
<213> ORGANISM: Human
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Thr Leu Glu Gln Gln His Xaa Val Ala Gln Gly Gln Trp
1               5                   10

<210> SEQ ID NO 4
<211> LENGTH: 16
<212> TYPE: PRT
<213> ORGANISM: Human

<400> SEQUENCE: 4

Glu Val Asp Pro Gly Ser Ala Glu Leu Gln Lys Val Leu Gln Gly
1               5                   10                  15

Asp

<210> SEQ ID NO 5
<211> LENGTH: 14
<212> TYPE: PRT
<213> ORGANISM: Human

<400> SEQUENCE: 5

Glu Leu Ser Ser Lys Ala Asp Glu Ala Ser Glu Leu Ala Cys
1               5                   10
```